United States Patent
Choi et al.

(10) Patent No.: US 9,639,155 B2
(45) Date of Patent: May 2, 2017

(54) BIOSIGNAL INTERFACE APPARATUS AND OPERATION METHOD OF BIOSIGNAL INTERFACE APPARATUS

(71) Applicant: SAMSUNG ELECTRONICS CO., LTD., Suwon-si (KR)

(72) Inventors: Chang Mok Choi, Seoul (KR); Ui Kun Kwon, Hwaseong-si (KR); Sang Kon Bae, Seongnam-si (KR); Chi Sung Bae, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/204,238

(22) Filed: Mar. 11, 2014

(65) Prior Publication Data

US 2015/0054728 A1 Feb. 26, 2015

(30) Foreign Application Priority Data

Aug. 21, 2013 (KR) .......................... 10-2013-0099204

(51) Int. Cl.
| | |
|---|---|
| *G09G 5/00* | (2006.01) |
| *G06F 3/01* | (2006.01) |
| *A61B 5/06* | (2006.01) |
| *A61B 5/00* | (2006.01) |
| *A61B 5/0488* | (2006.01) |
| *A61B 5/053* | (2006.01) |

(52) U.S. Cl.
CPC .............. *G06F 3/015* (2013.01); *A61B 5/065* (2013.01); *A61B 5/681* (2013.01); *G06F 3/017* (2013.01); *A61B 5/0488* (2013.01); *A61B 5/053* (2013.01); *A61B 5/6824* (2013.01); *A61B 5/6831* (2013.01)

(58) Field of Classification Search
USPC ........ 345/156, 158, 157, 173; 358/497, 1.14
See application file for complete search history.

(56) References Cited

U.S. PATENT DOCUMENTS

| | | | | |
|---|---|---|---|---|
| 7,333,090 | B2 * | 2/2008 | Tanaka et al. | ................ 345/158 |
| 7,545,524 | B2 * | 6/2009 | Seo | ..................... H04N 1/32609 |
| | | | | 358/1.14 |
| 2004/0068409 | A1 * | 4/2004 | Tanaka et al. | ................ 704/272 |
| 2005/0231770 | A1 * | 10/2005 | Seo | ..................... H04N 1/32609 |
| | | | | 358/497 |
| 2006/0121958 | A1 | 6/2006 | Jung et al. | |
| 2009/0327171 | A1 | 12/2009 | Tan et al. | |
| 2011/0054360 | A1 | 3/2011 | Son et al. | |
| 2012/0188158 | A1 * | 7/2012 | Tan et al. | ...................... 345/156 |

(Continued)

FOREIGN PATENT DOCUMENTS

| | | |
|---|---|---|
| JP | 7-248873 A | 9/1995 |
| KR | 10-2009-0030105 A | 3/2009 |

(Continued)

OTHER PUBLICATIONS

Extended European Search Report mailed Jan. 26, 2015 in European Application No. 14164319.7 (6 Pages).

*Primary Examiner* — Thuy Pardo
(74) *Attorney, Agent, or Firm* — NSIP Law

(57) ABSTRACT

A biosignal interface apparatus includes a sensor configured to detect a target in contact with the sensor, a position identifier configured to identify a position of the sensor on the target, and a controller configured to control an operation mode of the sensor based on the identified position.

18 Claims, 4 Drawing Sheets

(56) References Cited

U.S. PATENT DOCUMENTS

2012/0249409 A1* 10/2012 Toney et al. .................. 345/156
2013/0150697 A1   6/2013 Iami et al.
2013/0317648 A1* 11/2013 Assad .......................... 700/258

FOREIGN PATENT DOCUMENTS

| | | |
|---|---|---|
| KR | 10-2011-0040165 A | 4/2011 |
| KR | 10-2011-0056022 A | 5/2011 |
| KR | 10-2011-0062558 A | 6/2011 |
| KR | 10-2012-0064921 A | 6/2012 |
| KR | 10-2012-0064922 A | 6/2012 |
| WO | WO 2009/044967 A1 | 4/2009 |
| WO | WO 2011/133240 A1 | 10/2011 |

* cited by examiner

AREA OF BRACELET AT INITIAL POSITION <
AREA OF BRACELET AT FIRST POSITION

AREA OF BRACELET AT INITIAL POSITION >
AREA OF BRACELET AT SECOND POSITION

BIOSIGNAL INTERFACE APPARATUS AND OPERATION METHOD OF BIOSIGNAL INTERFACE APPARATUS

CROSS-REFERENCE TO RELATED APPLICATION

This application claims the benefit under 35 USC 119(a) of Korean Patent Application No. 10-2013-0099204, filed on Aug. 21, 2013, in the Korean Intellectual Property Office, the entire disclosure of which is incorporated herein by reference for all purposes.

BACKGROUND

1. Field

The following description relates to a biosignal interface apparatus and an operation method of the biosignal interface apparatus.

2. Description of Related Art

A biosensor may refer to an apparatus used to obtain biological information from a target and convert the information into a recognizable signal such as color, fluorescence, and an electrical signal. When the information obtained from the target is a biosignal, for example, an electromyography (EMG), the biosensor may convert muscle contraction or muscle relaxation of the target, for example, a human being, into a signal waveform based on the biosignal.

A bracelet type device including the biosensor may recognize a gesture of a finger, a wrist, and the like, and be used as a user interface to an external device. The bracelet type device may increase/decrease types of recognized gestures in proportion to a number of signals involved in a gesture recognition process.

The number of signals may be flexibly changed based on a position of the biosensor on the target to which the biosensor is to be attached. Accordingly, there is a desire for a model that may flexibly change the position of the biosensor on the target to which the biosensor is to be attached, properly adjust a number of biosignals to be detected, and effectively control an external device.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a biosignal interface apparatus, including a sensor configured to detect a target in contact with the sensor, a position identifier configured to identify a position of the sensor on the target, and a controller configured to control an operation mode of the sensor based on the identified position.

The controller may be configured to control the operation mode of the sensor based on a platform or an application controlled by a signal or a gesture detected by the sensor.

The controller may be configured to determine a number of signals or a number of gestures allowed to be detected by the sensor, and control the operation mode of the sensor to be in a mode in which the sensor detects the determined number of signals or the determined number of gestures.

The sensor may be configured to be in a form of a bracelet, and the position identifier may be configured to identify the position of the sensor based on a degree of deformation of the bracelet.

In response to the position identifier identifying a first position at which a contact area between the bracelet and the target is deformed to increase, the controller may be configured to increase a number of signals or a number of gestures allowed to be detected by the sensor, and control the operation mode of the sensor to be a mode in which the sensor detects the increased number of signals or the increased number of gestures.

In response to the position identifier identifying a second position at which a contact area between the bracelet and the target is deformed to decrease, the controller may be configured to decrease a number of signals or a number of gestures allowed to be detected by the sensor, and control the operation mode of the sensor to be a mode in which the sensor detects the decreased number of signals or the decreased number of gestures.

The sensor may be configured to be in a form of an elastic material, and the position identifier may be configured to identify the position of the sensor based on a degree of elasticity of the elastic material.

In response to the position identifier identifying a first position at which the elastic material is extended, the controller may be configured to increase a number of signals or a number of gestures allowed to be detected by the sensor, and control the operation mode of the sensor to be a mode in which the sensor detects the increased number of signals or the increased number of gestures.

In response to the position identifier identifying a second position at which the elastic material is contracted, the controller may be configured to decrease a number of signals or a number of gestures allowed to be detected by the sensor, and control the operation mode of the sensor to be a mode in which the sensor detects the decreased number of signals or the decreased number of gestures.

In another general aspect, there is provided an operation method of a biosignal interface apparatus, the method including identifying a position of a sensor on a target, and controlling an operation mode of the sensor based on the identified position.

The controlling may include controlling the operation mode of the sensor based on a platform or an application controlled by a signal or a gesture detected by the sensor.

The controlling may include determining a number of signals or a number of gestures allowed to be detected by the sensor, and controlling the operation mode of the sensor to be in a mode in which the sensor detects the determined number of signals or the determined number of gestures.

The sensor may be in a form of a bracelet and in contact with the target, and the identifying includes identifying the position of the sensor based on a degree of deformation of the bracelet.

The controlling may include increasing a number of signals or a number of gestures allowed to be detected by the sensor, and controlling the operation mode of the sensor to be a mode in which the sensor detects the increased number of signals or the increased number of gestures, in response to identifying a first position at which a contact area between the bracelet and the target is deformed to increase, and decreasing a number of signals or a number of gestures allowed to be detected by the sensor, and controlling the operation mode of the sensor to be a mode in which the sensor detects the decreased number of signals or the decreased number of gestures, in response to identifying a second position at which the contact area between the bracelet and the target is deformed to decrease.

The sensor may be in a form of an elastic material and in contact with the target, and the identifying may include identifying the position of the sensor based on a degree of elasticity of the elastic material.

The controlling may include increasing a number of signals or a number of gestures allowed to be detected by the sensor, and controlling the operation mode of the sensor to be a mode in which the sensor detects the increased number of signals or the increased number of gestures, in response identifying a first position at which the elastic material is extended, and decreasing a number of signals or a number of gestures allowed to be detected by the sensor, and controlling the operation mode of the sensor to be a mode in which the sensor detects the decreased number of signals or the decreased number of gestures, in response to identifying a second position at which the elastic material is contracted.

In still another general aspect, there is provided a biosignal interface apparatus including a sensor configured to detect a target, and be a bracelet, and a position identifier configured to identify a position of the sensor based on a characteristic of the bracelet.

The characteristic may be a contact area between the bracelet and the target.

The characteristic may be a circumference of the bracelet.

The biosignal interface apparatus may further include a controller configured to control a number of signals or a number of gestures allowed to be detected by the sensor, based on the identified position.

Other features and aspects will be apparent from the following detailed description, the drawings, and the claims.

Figure 1:
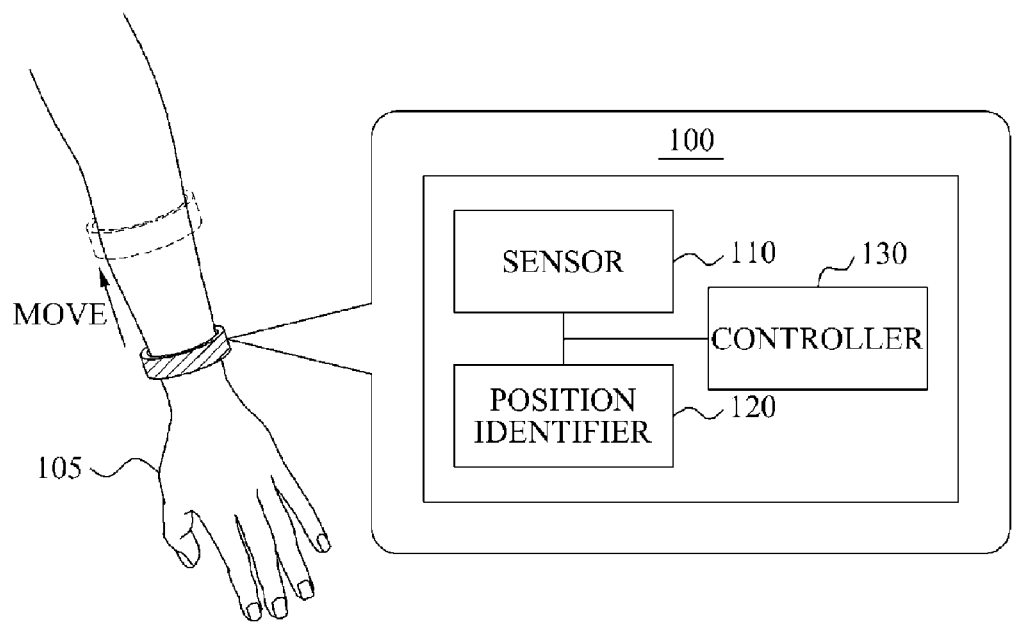
FIG. 1 is a diagram illustrating an example of a configuration of a biosignal interface apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

As described herein, a sensor may refer to a sensor or a set of sensors that may be attached to a target to detect a signal generated from the target. The detected signal may be a biosignal of biological information of the target. The sensor may include, for example, a biosensor, that may monitor the biological information, such as, muscle contraction or muscle relaxation occurring in the target, and detect the biosignal.

The sensor may be provided in a form of a bracelet fastened onto a body part of a human being or in a form of an elastic material capable of being flexibly extended and contracted by an external force. According to an example, the sensor may be provided in a form of an elastic bracelet.

For example, when the target is a muscle inside a lower part of an arm, the bracelet may be fastened onto a wrist, and the sensor provided in the bracelet may detect a signal generated from the muscle inside the lower part of the arm. Also, when the bracelet is elastic, the bracelet positioned on the wrist may be extended to move toward a forearm, and detect a signal generated from the muscle inside the lower part of the arm. A region of the wrist may have a relatively lower number of muscles distributed therein than a region of the forearm. Accordingly, the movement of the bracelet may enable the sensor to detect a relatively greater number of signals on the forearm than on the wrist.

According to an example, a biosignal interface apparatus may control a mode of the sensor based on a position of the sensor on the target toward which the sensor moves, and change a number of signals to be detected by the sensor. The biosignal interface apparatus may detect an optimum number of signals for an external platform or an application to be controlled, for energy efficiency.

FIG. 1 is a diagram illustrating an example of a configuration of a biosignal interface apparatus 100. Referring to FIG. 1, the biosignal interface apparatus 100 includes a sensor 110, a position identifier 120, and a controller 130.

The sensor 110 may be in contact with a target 105, and detect the target 105. The sensor 110 may detect at least one signal generated from the target 105. The target 105 may be a muscle of a living object from which detection of a biosignal is needed, and include a wrist muscle or a forearm muscle positioned inside a lower part of an arm.

The sensor 110 may include at least one sensor collecting the signal generated from the muscle as the target 105, and detect, using the at least one sensor, the signal generated from the muscle. The signal may be a bio-electric/magnetic signal, a bio-impedance signal, a bio-mechanical signal, and/or other signals known to one of ordinary skill in the art, which are generated in association with the muscle.

The sensor 110 may detect a gesture of the target 105, based on a pattern of the detected signal. For example, the sensor 110 may identify a difference among patterns of detected signals, and differently detect a gesture performed when a user makes a first or folds several fingers.

The sensor 110 may include the at least one sensor arranged at regular intervals from one another and provided in a form of a bracelet. When the bracelet is fastened onto the target 105, a sensing surface of the sensor 110 may be configured to be in contact with the target 105. The sensing surface may be a surface on which the at least one sensor is in direct contact with the target 105 and is capable of directly detecting the signal generated from the target 105. For example, the bracelet may detect, using the sensor 110, the signal, for example, a bio-electric/magnetic signal, a bio-impedance signal, a bio-mechanical signal, and/or other signals known to one of ordinary skill in the art, which are generated in association with the target 105.

The bracelet may be fastened by being wrapped around a skin on a muscle inside the lower part of an arm, although the bracelet may be fastened by covering the muscle inside the lower part of the arm with an area, for example, the sensing surface, of the bracelet in which the sensor 110 is arranged. The sensor 110 may collect, using the at least one sensor, a signal generated throughout the muscle, as a whole, which is inside the lower part of the arm as the target 105.

Also, the sensor 110 may be provided in a form of an elastic material capable of being extended or contracted by an external force. The sensor 110 may be easily attached to the target 105, using an elasticity of the elastic material, based on a type of the target 105.

The elastic material may refer to a material possessing elasticity, in detail, a property of being deformed outwardly by an external force and returning to an original form when the external force is removed. The elastic material may be manufactured with material such as rubber or a fabric.

For example, when the sensor 110 is provided in the form of the elastic material, the sensor 110 may detect the signal generated from the muscle inside the lower part of the arm as the target 105, and may detect a signal of the forearm muscle as the target 105 when the sensor 110 moves toward the forearm by a force applied as a result of an active decision of the user. The elastic material may be extended so that the sensor 110 may be attached to an area of the forearm having a thicker circumference than the wrist.

According to an example, the sensor 110 may be provided in a form of an elastic bracelet capable of being extended and contracted by an external force. The sensor 110 may be attached to the target 105, using an elasticity characteristic without assistance from an additional fastening tool, while changing a position on the target 105 to an arbitrary position on the target 105. For convenience of description, an example in which the sensor 110 is provided in the form of the elastic bracelet will be described hereinafter.

The position identifier 120 identifies the position of the sensor 110 on the target 105. The position identifier 120 may identify the position of the sensor 110 based on a degree of elasticity of the elastic bracelet.

For example, when the bracelet is initially on the wrist, a circumference of the bracelet that is needed to be fastened onto the wrist is "$\alpha$", and a circumference of the bracelet that is newly needed due to a movement is greater than "$\alpha$", the position identifier 120 may identify that the bracelet moves in a direction toward the forearm, which is thicker than the wrist. In this example, "$\alpha$" is a value denoting a length, for example, 1 millimeter (mm) or 1 centimeter (cm). When the bracelet is extended as described in the foregoing, the position identifier 120 may identify a position on the target 105 to which the sensor 110 is attached as a first position.

Similarly, when the bracelet is initially on the forearm, and a circumference of the bracelet that is needed to be fastened onto the wrist is "$\alpha$", and a circumference of the bracelet that is newly needed due to a movement is less than "$\alpha$", the position identifier 120 may identify that the bracelet moves in a direction toward the wrist, which is thinner than the forearm. When the bracelet is contracted as described in the foregoing, the position identifier 120 may identify a position on the target 105 to which the sensor 110 is attached as a second position.

In another example of identifying the position of the sensor 110, the position identifier 120 may identify the position of the sensor 110 based on a degree of deformation of the bracelet. For example, the position identifier 120 may identify a first position at which a contact area between the bracelet and the target 105 is deformed to increase. That is, when the bracelet is initially on the wrist, a contact area between the bracelet and the wrist is "$\beta$", and a contact area between the bracelet and the forearm that is newly measured after a movement is greater than "$\beta$", the position identifier 120 may identify that the bracelet moves in the direction toward the forearm having a greater surface area than the wrist. In this example, "$\beta$" is a value denoting an area, for example, 1 mm$^2$ or 1 cm$^2$. When the bracelet is deformed to increase as described in the foregoing, the position identifier 120 may identify a position on the target 105 to which the sensor 110 is attached as the first position.

In another example, the position identifier 120 may identify a second position at which the contact area between the bracelet and the target 105 is deformed to decrease. That is, when the bracelet is initially on the forearm, a contact area between the bracelet and the wrist is "$\beta$", and a contact area between the bracelet and the forearm that is newly measured after a movement is less than "$\beta$", the position identifier 120 may identify that the bracelet moves in the direction toward the wrist having a smaller surface area than the forearm. When the bracelet is deformed to decrease as described in the foregoing, the position identifier 120 may identify a position on the target 105 to which the sensor 110 is attached as the second position.

The controller 130 controls a mode of the sensor 110 based on the identified position. The controller 130 flexibly changes a number of signals allowed to be detected by the sensor 110 based on the position of the bracelet on the target 105 that is identified by the position identifier 120.

For example, the position identifier 120 and/or the controller 130 may monitor, using a strain gauge, a degree of an extension of the bracelet. As a result of the monitoring, when the extension of the bracelet is greater than a predetermined reference value, the controller 130 may control the mode of the sensor 110 to be an arbitrary mode 1. When the extension of the bracelet is less than or equal to the reference value, the controller 130 may control the mode of the sensor 110 to be an arbitrary mode 2 differing from the arbitrary mode 1.

The controller 130 may control the mode of the sensor 110 based on a platform or an application controlled by a signal or a gesture collected by the sensor 110. The platform may refer to hardware and/or software controlled by the signal and fundamental to an external device and/or a computer.

For example, when a number of control types needed for an image platform is two, including power ON/OFF and volume up/down, the controller 130 may control the mode of the sensor 110 to be a mode in which the sensor 110 detects a number of signals capable of generating at least two control types. In another example, when a number of control types needed for a game application is four, including shoot, reload, fire consecutive shots, and bomb release, the controller 130 may control the mode of the sensor 110 to be a mode in which the sensor 110 detects a number of signals capable of generating at least four control types.

Also, the controller 130 may determine a number of signals or a number of gestures allowed to be detected by the sensor 110, and control the mode of the sensor 110 to be a mode in which the sensor 110 detects the determined number of signals or the determined number of gestures. For example, for the image platform, when the power ON/OFF is controlled by a gesture of making a fist, and the volume up/down is controlled by a gesture of unfolding an index finger and a little finger, the controller 130 may control the mode of the sensor 110 to be a mode in which the sensor 110 detects a pattern of a signal or patterns of signals capable of identifying at least the gestures. In another example, for the game application, when the control type of shoot is controlled by a gesture of extending a thumb and an index finger, the control type of reload is controlled by a gesture of flexing a thumb, the control type of fire consecutive shots is controlled by a gesture of unfolding all fingers, and the control type of bomb release is controlled by a gesture of folding all fingers, the controller 130 may control the mode of the sensor 110 to be a mode in which the sensor 110 detects a pattern of a signal or patterns of signals capable of identifying at least the gestures.

The biosignal interface apparatus 100 may flexibly change the number of signals to be detected by the sensor 110 by proper control of the mode of the sensor 110 based on the position of the sensor 110, and enable control of various external devices. Also, the biosignal interface apparatus 100 may determine various modes of the sensor 110 based on a number of the control types to be controlled, and facilitate a formation of an optimum control environment in which power consumption of the sensor 110 is minimized. Hereinafter, a mode control by the controller 130 will be described by referring to FIGS. 2A through 3B.

Figure 2A:
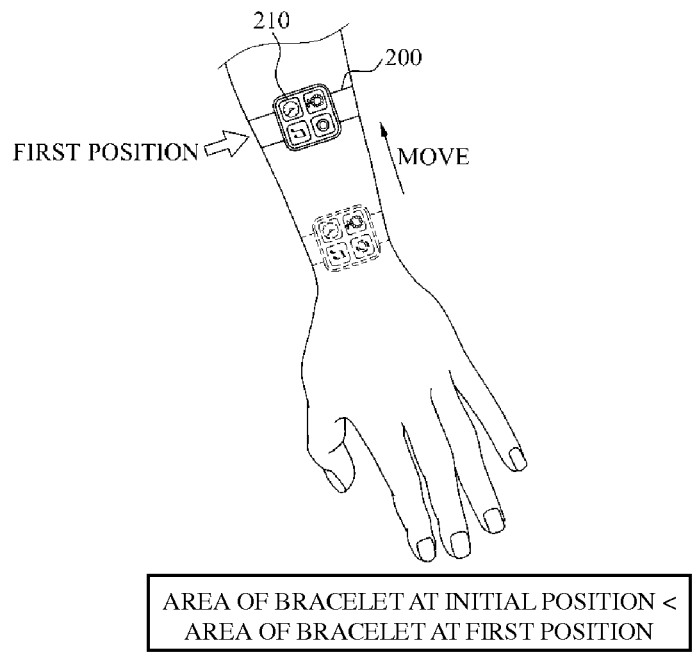
FIGS. 2A and 2B are diagrams illustrating examples of controlling a mode of a sensor.
Figure 2B:
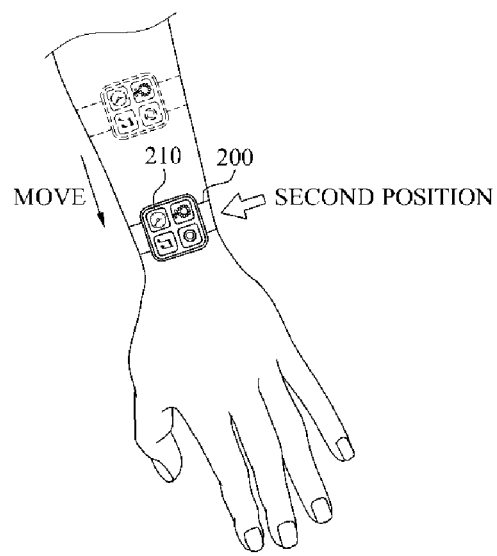

FIGS. 2A and 2B are diagrams illustrating examples of controlling a mode of a sensor 210. FIGS. 2A and 2B illustrate examples of identifying a position of the sensor 210, and controlling the mode of the sensor 210 based on a degree of deformation of a bracelet 200 provided with the sensor 210. A sensor capable of detecting a physical form of the bracelet 200 may include a strain gauge, a piezoelectric sensor, a pneumatic sensor, and/or other sensors known to one of ordinary skill in the art.

FIG. 2A illustrates an example in which the bracelet 200 moves from a wrist around which the bracelet 200 is initially positioned to a part of a forearm thicker than the wrist. A biosignal interface apparatus (e.g., 100 of FIG. 1) including the sensor 210 identifies a first position at which a contact area between the bracelet 200 and the wrist is deformed to increase.

In detail, the biosignal interface apparatus compares a contact area between the bracelet 200 and the wrist at an initial position to a contact area between the bracelet 200 and the forearm at the first position after the movement. As a result of the comparison, when the bracelet 200 is deformed, and the contact area of the bracelet 200 at the initial position is less than the contact area of the bracelet 200 at the first position, the biosignal interface apparatus determines to increase a number of signals or a number of gestures allowed to be detected by the sensor 210, and controls the mode of the sensor 210 to be a mode in which the sensor 210 detects the increased number of signals or the increased number of gestures. The biosignal interface apparatus may enable control of an external platform and an application that need a relatively greater number of control types.

FIG. 2B illustrates an example in which the bracelet 200 moves from the forearm around which the bracelet 200 is initially positioned to a part of the wrist thinner than the forearm. The biosignal interface apparatus identifies a second position at which the contact area between the bracelet 200 and the forearm is deformed to decrease.

In detail, the biosignal interface apparatus compares the contact area between the bracelet 200 and the forearm at the initial position to the contact area between the bracelet 200 and the wrist at the second position after the movement. As a result of the comparison, when the bracelet 200 is deformed, and the contact area of the bracelet 200 at the initial position is greater than the contact area of the bracelet 200 at the second position, the biosignal interface apparatus determines to decrease the number of signals or the number of gestures allowed to be detected by the sensor 210, and controls the mode of the sensor 210 to be a mode in which the sensor 210 detects the decreased number of signals or the decreased number of gestures.

The biosignal interface apparatus may control the mode of the sensor 210 to be a mode in which a relatively fewer number of controls are enabled after an operation of a platform or an application ends, and thus, reduce an amount of power supplied to the sensor 210. Accordingly, a total amount of power for the biosignal interface apparatus may be maintained for an optimal duration possible.

Figure 3A:
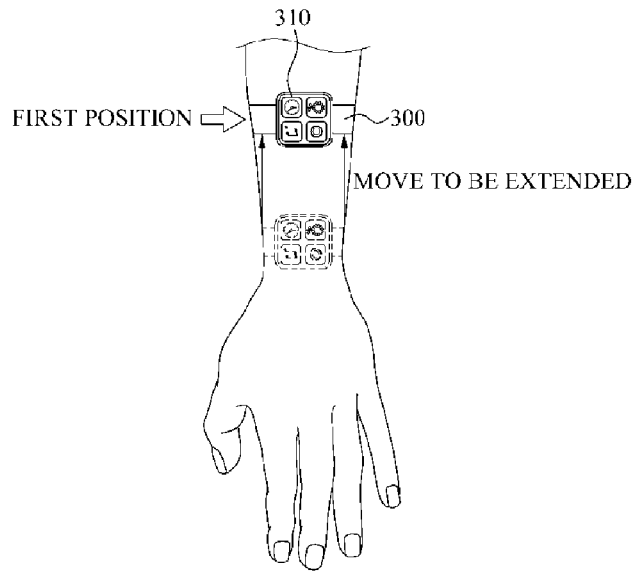
FIGS. 3A and 3B are diagrams illustrating other examples of controlling a mode of a sensor.
Figure 3B:
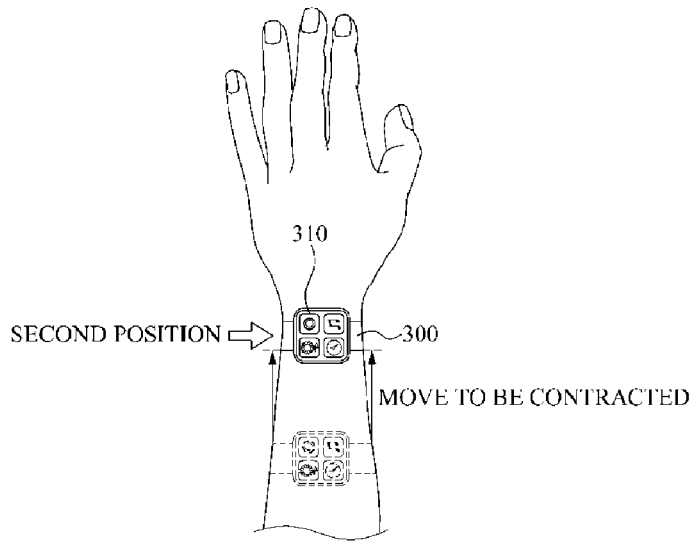

FIGS. 3A and 3B are diagrams illustrating other examples of controlling a mode of a sensor 310. FIGS. 3A and 3B illustrate examples of identifying a position of the sensor 310, and controlling the mode of the sensor 310 based on a degree of extension or contraction of an elastic material 300 provided with the sensor 310.

FIG. 3A illustrates an example in which the elastic material 300 moves from a wrist around which the elastic material 300 is initially positioned to a part of a forearm thicker than the wrist. A biosignal interface apparatus (e.g., 100 of FIG. 1) identifies a first position at which the elastic material 300 is extended to be greater than a length or circumference needed to be fastened onto the wrist.

In detail, the biosignal interface apparatus compares a length needed to fasten the elastic material 300 onto an initial position corresponding to the wrist to a length needed to fasten the elastic material 300 onto the first position corresponding to the forearm. As a result of the comparison, when the length of the elastic material 300 is extended, that is, the length of the elastic material 300 at the initial position is less than the length of the elastic material 300 at the first position, the biosignal interface apparatus determines to increase a number of signals or a number of gestures allowed to be detected by the sensor 310, and controls the mode of the sensor 310 to be a mode in which the sensor 310 detects the increased number of signals or the increased number of gestures. The biosignal interface apparatus may enable control of an external platform and an application that need a relatively greater number of control types.

FIG. 3B illustrates an example in which the elastic material 300 moves from the forearm around which the elastic material 300 is initially positioned to the wrist thinner than the forearm. The biosignal interface apparatus identifies a second position at which the elastic material 300 is contracted to be less than a length or circumference needed to be fastened onto the forearm.

In detail, the biosignal interface apparatus may compare the length needed to fasten the elastic material 300 onto the initial position corresponding to the forearm, to the length needed to fasten the elastic material 300 onto the second position corresponding to the wrist. As a result of the comparison, when the length of the elastic material 300 is contracted, that is, the length of the elastic material 300 at the initial position is greater than the length of the elastic material 300 at the second position, the biosignal interface apparatus determines to decrease the number of signals or the number of gestures allowed to be detected by the sensor 310, and controls the mode of the sensor 310 to be a mode in which the sensor 310 detects the decreased number of signals or the decreased number of gestures.

The biosignal interface apparatus may control the mode of the sensor 310 to be a mode in which a relatively fewer number of controls are enabled after an operation of a platform or an application ends, and thus, reduce an amount of power supplied to the sensor 310. Accordingly, a total power for the biosignal interface apparatus may be maintained for an optimal duration possible. Hereinafter, a flowchart of an operation method of the biosignal interface apparatus 100 of FIG. 1 will be described in greater detail.

Figure 4:
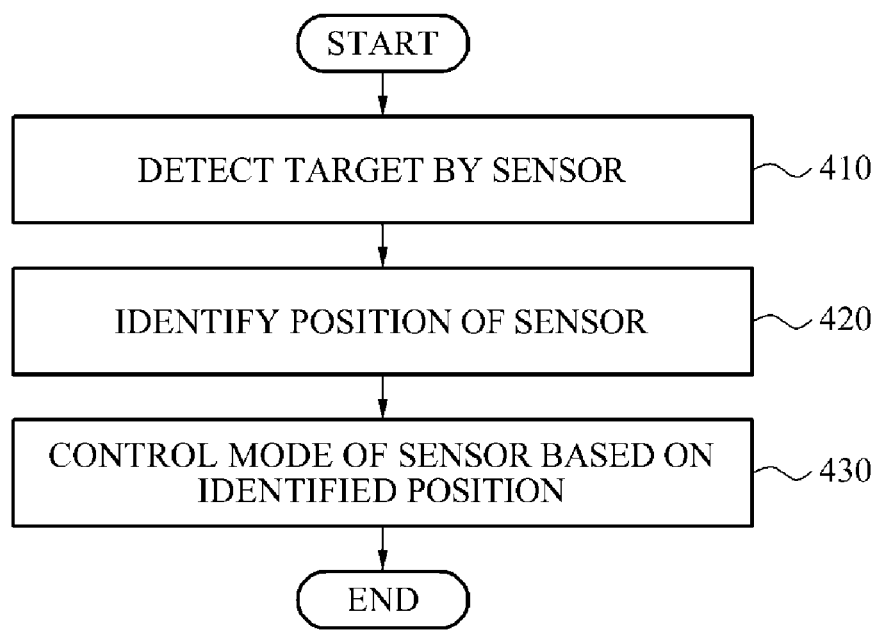
FIG. 4 is a flowchart illustrating an example of an operation method of a biosignal interface apparatus.

FIG. 4 is a flowchart illustrating an example of an operation method of the biosignal interface apparatus 100. According to the example, the biosignal interface apparatus 100 may approximately estimate a portion of a lower part of an arm on which the sensor 110 of FIG. 1 is positioned based on a thickness of the lower part of the arm being thicker in a direction toward a forearm and elbow than in a direction toward a wrist. The biosignal interface apparatus 100 may also change a mode of, for example, a number of recognizable gestures.

In operation 410, the biosignal interface apparatus 100 detects the target 105 of FIG. 1 in contact with the sensor 110 by using the sensor 110. The sensor 110 may detect at least one signal generated from the target 105. The target 105 may be a muscle of a living object from which detection of a biosignal is needed, and include a wrist muscle or a forearm muscle positioned inside the lower part of the arm.

The biosignal interface apparatus 100 may detect, using at least one sensor, the signal generated from the muscle as the target 105. The signal may be a bio-electric/magnetic signal, a bio-impedance signal, a bio-mechanical signal, and/or other signals known to one of ordinary skill in the art, which are generated in association with the muscle.

The biosignal interface apparatus 100 may detect, using the sensor 110, a gesture of the target 105, based on patterns of signals detected by the sensor 110. For example, the biosignal interface apparatus 100 may identify a difference among the patterns of the detected signals, and differently detect a gesture performed when a user makes a first and a gesture performed when the user folds some fingers.

The sensor 110 may be provided in a form of a bracelet in which the at least one sensor is arranged at regular intervals. When the bracelet is fastened onto the target 105, a sensing surface of the sensor 110 may be configured to be in contact with the target 105. The sensing surface may be a surface on which the at least one sensor is in contact with the target 105 and is directly detecting the signal generated from the target 105. For example, the bracelet may detect, using the sensor 110, the signal, for example, a bio-electric/magnetic signal, a bio-impedance signal, a bio-mechanical signal, and/or other signals known to one of ordinary skill in the art, which are generated in association with the target 105.

The bracelet may be fastened onto the target 105 by wrapping around a skin on a muscle inside the lower part of the arm, although the bracelet may be fastened onto the target 105 by covering the muscle inside the lower part of the arm with an area, for example, the sensing surface, of the bracelet in which the sensor 110 is arranged. The sensor 110 may detect, using the at least one sensor, a signal generated throughout an entirety of the muscle inside the lower part of the arm that corresponds to the target 105.

The sensor 110 may be provided in a form of an elastic material capable of being extended or contracted by an external force. The sensor 110 may be easily attached to the target 105, using an elasticity characteristic of the elastic material, based on a type of the target 105.

The elastic material may refer to a material possessing elasticity, in detail, a property of being deformed outwardly by the external force and returning to an original form when the external force is removed. The elastic material may be manufactured with a material such as rubber or a fabric.

When the sensor 110 is provided in the form of the elastic material, the sensor 110 may detect the signal generated from the muscle inside the lower part of the arm as the target 105, and detect the signal of the forearm muscle as the target 105 when the sensor 110 moves toward the forearm by a force applied as a result of an active decision of the user. The elastic material may be extended so that the sensor 110 may be attached to the forearm thicker than the wrist in circumference.

The sensor 110 may be provided in a form of an elastic bracelet capable of being extended and contracted by an external force. The sensor 110 may be attached to the target 105, using elasticity without an aid of an additional fastening tool, while changing a position on the target 105 to an arbitrary position on the target 105.

In operation 420, the biosignal interface apparatus 100 identifies a position of the sensor 110 on the target 105. The biosignal interface apparatus 100 may identify the position of the sensor 110 based on a degree of extension or contraction of the elastic bracelet.

For example, when the bracelet is initially on the wrist, a circumference of the bracelet that is needed to be fastened onto the wrist is "α", and a circumference of the bracelet that is newly needed for a movement is extended to be greater than "α", it may be confirmed that the bracelet moves to the forearm thicker than the wrist. When the bracelet is extended as described in the foregoing, the biosignal interface apparatus 100 may identify the position of the sensor 110 on the target 105 to be a first position.

Similarly, when the bracelet is initially on the forearm, a circumference of the bracelet that is needed to be fastened onto the forearm is "α", and a circumference that is newly needed for a movement is contracted to be less than "α", it may be confirmed that the bracelet moves to the wrist thinner than the forearm. When the bracelet is contracted as described in the foregoing, the biosignal interface apparatus 100 may identify the position of the sensor 110 on the target 105 to be a second position.

In another example of identifying the position of the sensor 110, the biosignal interface apparatus 100 may identify the position of the sensor 110 based on a degree of deformation of the bracelet. For example, the biosignal interface apparatus 100 may identify the first position at which a contact area between the bracelet and the target 105 is deformed to increase. That is, when the bracelet is initially on the wrist, a contact area between the bracelet and the wrist is "β", and a contact area between the bracelet and the forearm that is newly measured after a movement is greater than "β", it may be confirmed that the bracelet moves in a direction toward the forearm having a greater surface area than the wrist. When the bracelet is deformed to increase as described in the foregoing, the biosignal interface apparatus 100 may identify the position of the sensor 110 on the target 105 to be the first position.

In another example, the biosignal interface apparatus 100 may identify a second position at which the contact area between the bracelet and the target 105 is deformed to decrease. That is, when the bracelet is initially on the forearm, the contact area between the bracelet and the wrist is "β", and the contact area between the bracelet and the forearm that is newly measured after a movement is less than "β", it may be confirmed that the bracelet moves in a direction toward the wrist having a smaller a surface area than the forearm. When the bracelet is deformed to decrease as described in the foregoing, the biosignal interface apparatus 100 may identify the position of the sensor 110 on the target to be the second position.

In operation 430, the biosignal interface apparatus 100 controls a mode of the sensor 110 based on the identified position. The biosignal interface apparatus 100 flexibly changes a number of signals to be received by the sensor 110 based on the identified position of the bracelet on the target 105.

The biosignal interface apparatus 100 may control the mode of the sensor 110 based on a platform or an application controlled by a signal or a gesture detected by the sensor 110. The platform may refer to hardware and/or software controlled by the signal and fundamental to operation of an external device and/or a computer.

For example, when a number of control types to be controlled in an image platform is two, including power ON/OFF and volume up/down, the biosignal interface apparatus 100 may control the mode of the sensor 110 to be a mode in which the sensor 110 detects a number of signals capable of generating at least two control types. In another example, when a number of control types to be controlled in a game application is four, including shoot, reload, fire consecutive shots, and bomb release, the biosignal interface apparatus 100 may control the mode of the sensor 110 to be a mode in which the sensor 110 detects a number of signals capable of generating at least four control types.

The biosignal interface apparatus 100 may determine a number of signals or a number of gestures allowed to be detected by the sensor 110, and control the mode of the sensor 110 to be a mode in which the sensor 110 detects the determined number of signals or the determined number of gestures. For example, in the image platform, when the power ON/OFF is controlled by a gesture of making a fist, and the volume up/down is controlled by a gesture of flexing an index finger and a little finger, the biosignal interface apparatus 100 may control the mode of the sensor 110 to be a mode in which the sensor 110 detects a pattern of a signal or patterns of signals capable of identifying at least the gestures. In another example, in the game application, when the control type of shoot is controlled by a gesture of extending a thumb and an index finger, the control type of reload is controlled by a gesture of flexing a thumb, the control type of fire consecutive shots is controlled by a gesture of unfolding all fingers, and the control type of bomb release is controlled by a gesture of folding all fingers, the biosignal interface apparatus 100 may control the mode of the sensor 110 to be a mode in which the sensor 110 detects a pattern of a signal or patterns of signals capable of identifying at least the gestures.

The biosignal interface apparatus 100 may flexibly change the number of signals to be detected by the sensor 110 by properly controlling the mode of the sensor 110 based on the position of the sensor 110, and enable control of various external devices. Also, the biosignal interface apparatus 100 may determine various modes of the sensor 110 based on a number of the control types to be controlled, and facilitate a formation of an optimum control environment in which power consumption of the sensor 110 is minimized.

The various elements and methods described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

As a non-exhaustive illustration only, a device described herein may refer to mobile devices such as, for example, a cellular phone, a smart phone, a wearable smart device (such as, for example, a ring, a watch, a pair of glasses, a bracelet, an ankle bracket, a belt, a necklace, an earring, a headband, a helmet, a device embedded in the cloths or the like), a personal computer (PC), a tablet personal computer (tablet), a phablet, a personal digital assistant (PDA), a digital camera, a portable game console, an MP3 player, a portable/personal multimedia player (PMP), a handheld e-book, an ultra mobile personal computer (UMPC), a portable lab-top PC, a global positioning system (GPS) navigation, and devices such as a high definition television (HDTV), an optical disc player, a DVD player, a Blue-ray player, a setup box, or any other device capable of wireless communication or network communication consistent with that disclosed herein. In a non-exhaustive example, the wearable device may be self-mountable on the body of the user, such as, for example, the glasses or the bracelet. In another non-exhaustive example, the wearable device may be mounted on the body of the user through an attaching device, such as, for example, attaching a smart phone or a tablet to the arm of a user using an armband, or hanging the wearable device around the neck of a user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal interface apparatus, comprising:
a sensor configured to detect a body part of a target in contact with the sensor;
a position identifier configured to identify a position based on movement of the sensor on the body part of the target on which the sensor disposed on due to a change in length of the sensor; and
a controller configured to control an operation mode of the sensor to be in a mode in which the controller adaptively changes a number of signals or gestures allowed to be detected by the sensor, based on the identified position, thereby minimizing power consumption,
wherein the controller is configured to control the operation mode of the sensor to be in a mode in which the sensor detects the changed number of signals or gestures.

2. The apparatus of claim 1, wherein the controller is configured to control the operation mode of the sensor based on a platform or an application controlled by a signal or a gesture detected by the sensor.

3. The apparatus of claim 1, wherein:
the sensor is configured to be in a form of a bracelet; and
the position identifier is configured to identify the position of the sensor based on a degree of deformation of the bracelet.

4. The apparatus of claim 3, wherein, in response to the position identifier identifying a first position at which a contact area between the bracelet and the target is deformed to increase, the controller is configured to:
increase a number of signals or a number of gestures allowed to be detected by the sensor; and
control the operation mode of the sensor to be a mode in which the sensor detects the increased number of signals or the increased number of gestures.

5. The apparatus of claim 3, wherein, in response to the position identifier identifying a second position at which a contact area between the bracelet and the target is deformed to decrease, the controller is configured to:
decrease a number of signals or a number of gestures allowed to be detected by the sensor; and
control the operation mode of the sensor to be a mode in which the sensor detects the decreased number of signals or the decreased number of gestures.

6. The apparatus of claim 1, wherein:
the sensor is configured to be in a form of an elastic material; and
the position identifier is configured to identify the position of the sensor based on a degree of elasticity of the elastic material.

7. The apparatus of claim 6, wherein, in response to the position identifier identifying a first position at which the elastic material is extended, the controller is configured to:
increase a number of signals or a number of gestures allowed to be detected by the sensor; and
control the operation mode of the sensor to be a mode in which the sensor detects the increased number of signals or the increased number of gestures.

8. The apparatus of claim 6, wherein, in response to the position identifier identifying a second position at which the elastic material is contracted, the controller is configured to:
decrease a number of signals or a number of gestures allowed to be detected by the sensor; and
control the operation mode of the sensor to be a mode in which the sensor detects the decreased number of signals or the decreased number of gestures.

9. An operation method of a biosignal interface apparatus, the method comprising:
identifying a position based on movement of the sensor on a body part of a target on which a sensor is disposed on, the position being identified based on a change in length of the sensor; and
controlling an operation mode of the sensor to be in a mode that adaptively changes a number of signals or gestures allowed to be detected by the sensor, based on the identified position, thereby minimizing power consumption,
wherein the controlling comprises controlling the operation mode of the sensor to be in a mode in which the sensor detects the determined number of signals or gestures.

10. The method of claim 9, wherein the controlling comprises:
controlling the operation mode of the sensor based on a platform or an application controlled by a signal or a gesture detected by the sensor.

11. The method of claim 9, wherein:
the sensor is in a form of a bracelet and in contact with the target; and
the identifying comprises identifying the position of the sensor based on a degree of deformation of the bracelet.

12. The method of claim 11, wherein the controlling comprises:
increasing a number of signals or a number of gestures allowed to be detected by the sensor, and controlling the operation mode of the sensor to be a mode in which the sensor detects the increased number of signals or the increased number of gestures, in response to identifying a first position at which a contact area between the bracelet and the target is deformed to increase; and
decreasing a number of signals or a number of gestures allowed to be detected by the sensor, and controlling the operation mode of the sensor to be a mode in which the sensor detects the decreased number of signals or the decreased number of gestures, in response to identifying a second position at which the contact area between the bracelet and the target is deformed to decrease.

13. The method of claim 9, wherein:
the sensor is in a form of an elastic material and in contact with the target; and
the identifying comprises identifying the position of the sensor based on a degree of elasticity of the elastic material.

14. The method of claim 13, wherein the controlling comprises:
increasing a number of signals or a number of gestures allowed to be detected by the sensor, and controlling the operation mode of the sensor to be a mode in which the sensor detects the increased number of signals or the increased number of gestures, in response identifying a first position at which the elastic material is extended; and
decreasing a number of signals or a number of gestures allowed to be detected by the sensor, and controlling the operation mode of the sensor to be a mode in which the sensor detects the decreased number of signals or the decreased number of gestures, in response to identifying a second position at which the elastic material is contracted.

15. A biosignal interface apparatus, comprising:
a sensor configured to detect a body part of a target, and be a bracelet;
a position identifier configured to identify a position based on movement of the sensor on the body part of the target on which the sensor is disposed on to be in a mode that adaptively changes a number of signals or gestures allowed to be detected by the sensor, the position being identified based on a characteristic of the bracelet; and
a controller configured to control the mode of the sensor to be in a mode in which the sensor detects the changed number of signals or gestures.

16. The biosignal interface apparatus of claim 15, wherein the characteristic is a contact area between the bracelet and the target.

17. The biosignal interface apparatus of claim 15, wherein the characteristic is a circumference of the bracelet.

18. The biosignal interface apparatus of claim 15, further comprising:
a controller configured to control a number of signals or a number of gestures allowed to be detected by the sensor, based on the identified position.

* * * * *